United States Patent
Masada

(10) Patent No.: US 9,453,820 B2
(45) Date of Patent: Sep. 27, 2016

(54) CRACK AND THICKNESS DETECTING APPARATUS

(71) Applicant: DISCO CORPORATION, Tokyo (JP)

(72) Inventor: Takayuki Masada, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 187 days.

(21) Appl. No.: 14/339,687

(22) Filed: Jul. 24, 2014

(65) Prior Publication Data

US 2015/0027227 A1 Jan. 29, 2015

(30) Foreign Application Priority Data

Jul. 24, 2013 (JP) .................................. 2013-153264

(51) Int. Cl.
*G01N 29/07* (2006.01)
*G01B 17/02* (2006.01)

(52) U.S. Cl.
CPC ............... *G01N 29/07* (2013.01); *G01B 17/02* (2013.01); *G01N 2291/02854* (2013.01); *G01N 2291/044* (2013.01); *G01N 2291/2697* (2013.01)

(58) Field of Classification Search
CPC ...................... G01N 29/07; G01N 2291/2697; G01N 2291/044; G01N 2291/02854; G01B 17/02
USPC .......................................................... 73/598
See application file for complete search history.

(56) References Cited

U.S. PATENT DOCUMENTS

| | | | | |
|---|---|---|---|---|
| 6,198,294 B1* | 3/2001 | Black | ...................... | G01B 7/08 324/663 |
| 7,233,401 B1* | 6/2007 | Houser | .............. | G01B 11/0625 356/503 |
| 2004/0007257 A1* | 1/2004 | Park | .......................... | B08B 3/12 134/95.2 |
| 2005/0017880 A1* | 1/2005 | Joshi | ....................... | H03M 7/14 341/50 |

FOREIGN PATENT DOCUMENTS

| | | | |
|---|---|---|---|
| JP | 2005-153090 | | 6/2005 |
| JP | 2007199013 | * | 8/2007 |
| JP | 2009111238 | * | 5/2009 |
| JP | 2011-146568 | | 7/2011 |

* cited by examiner

*Primary Examiner* — J M Saint Surin
(74) *Attorney, Agent, or Firm* — Greer Burns & Crain, Ltd.

(57) ABSTRACT

A crack and thickness detecting apparatus for detecting a crack in a wafer and also detecting the thickness of the wafer. The apparatus includes an ultrasonic oscillating unit oscillating a first ultrasonic wave toward the upper surface of the wafer at a predetermined incident angle, an ultrasonic oscillating and receiving unit oscillating a second ultrasonic wave toward the upper surface of the wafer in a direction perpendicular thereto and also receiving reflected waves obtained by the reflection of the first and second ultrasonic waves from the wafer, a crack determining unit determining whether or not the crack is present in the wafer according to the first reflected wave, and a thickness calculating unit calculating the thickness of the wafer according to the second reflected wave. The ultrasonic oscillating and receiving unit alternately receives the first reflected wave and the second reflected wave.

3 Claims, 7 Drawing Sheets

CRACK AND THICKNESS DETECTING APPARATUS

BACKGROUND OF THE INVENTION

1. Field of the Invention

The present invention relates to a crack and thickness detecting apparatus capable of detecting a crack in a wafer and the thickness of the wafer during griding of the wafer.

2. Description of the Related Art

In a semiconductor device fabrication process, a plurality of crossing division lines are formed on the front side of a wafer such as a semiconductor wafer to thereby partition a plurality of regions where a plurality of circuits such as ICs and LSIs are respectively formed. After the back side of the wafer is ground by a grinding apparatus to reduce the thickness of the wafer to a predetermined thickness, the wafer is cut along the division lines by a cutting apparatus to thereby obtain a plurality of individual device chips divided from each other. These device chips are packaged and widely used in electric equipment such as mobile phones and personal computers.

The grinding apparatus includes a chuck table for holding a wafer and a grinding wheel having a plurality of abrasive members arranged annularly, wherein the abrasive members of the grinding wheel being rotated are brought into contact with the back side of the wafer held on the chuck table (see Japanese Patent Laid-open No. 2005-153090, for example). During grinding of the wafer, there is a case that an unpredictable load may be applied to the wafer due to clogging of the abrasive members, falling of a lump of abrasive grains, a change in manner of supply of a grinding water, etc., causing the generation of fine cracks that cannot be visually identified. Such fine cracks cause device failure and it is therefore preferable to find the fine cracks after ending a grinding step. As an apparatus for detecting a crack in a wafer, there has been proposed an ultrasonic probe adapted to come into contact with the wafer (see Japanese Patent Laid-open No. 2011-146568, for example).

SUMMARY OF THE INVENTION

However, the apparatus described in Japanese Patent Laid-open No. 2011-146568 is an apparatus independent of the grinding apparatus. Further, the ultrasonic probe is so configured as to oscillate an ultrasonic wave in the condition that the wafer is attached thereto under suction, so that a crack in the wafer cannot be detected during grinding. On the other hand, it is necessary to measure the thickness of the wafer during grinding in real time. To detect a crack during grinding, a crack detecting apparatus must be provided in addition to a thickness detecting apparatus, causing an increase in equipment cost. A detecting apparatus capable of concurrently performing the crack detection and the thickness detection during grinding is not in existence.

It is therefore an object of the present invention to provide a crack and thickness detecting apparatus which can detect a crack in a wafer and the thickness of the wafer during grinding with an inexpensive configuration.

In accordance with an aspect of the present invention, there is provided a crack and thickness detecting apparatus for detecting a crack in a wafer held on a rotating chuck table and also detecting the thickness of the wafer, the crack and thickness detecting apparatus including: an ultrasonic oscillating unit oscillating a first ultrasonic wave toward the upper surface of the wafer held on the chuck table at a predetermined incident angle; an ultrasonic oscillating and receiving unit oscillating a second ultrasonic wave toward the upper surface of the wafer in a direction perpendicular thereto and also receiving the first ultrasonic wave and the second ultrasonic wave propagated and reflected in the wafer; a pulse voltage generating unit applying a pulse voltage to the ultrasonic oscillating unit and the ultrasonic oscillating and receiving unit; a crack determining unit determining whether or not the crack is present in the wafer from waveform information on the first ultrasonic wave received by the ultrasonic oscillating and receiving unit; and a thickness calculating unit calculating the thickness of the wafer from waveform information on the second ultrasonic wave received by the ultrasonic oscillating and receiving unit, wherein the ultrasonic oscillating unit and the ultrasonic oscillating and receiving unit alternately oscillate the first ultrasonic wave and the second ultrasonic wave to the wafer held on the rotating chuck table with a time difference, and the ultrasonic oscillating and receiving unit alternately receives the first ultrasonic wave and the second ultrasonic wave, the first ultrasonic wave oscillated by the ultrasonic oscillating unit and applied obliquely to the wafer is propagated in the wafer and irregularly reflected by the crack in the wafer, and the crack determining unit determines the presence of the crack in the wafer in the case that the ultrasonic oscillating and receiving unit receives a reflected wave obtained by the irregular reflection of the first ultrasonic wave, and the second ultrasonic wave oscillated by the ultrasonic oscillating and receiving unit and applied perpendicularly to the wafer is reflected on the upper surface of the wafer to generate an upper surface reflected wave, propagated in the wafer and also reflected on the lower surface of the wafer to generate a lower surface reflected wave, and the thickness calculating unit calculates the thickness of the wafer from a time difference between the reception of the upper surface reflected wave and the reception of the lower surface reflected wave by the ultrasonic oscillating and receiving unit.

With this configuration, the first ultrasonic wave is oscillated by the ultrasonic oscillating unit toward the upper surface of the wafer at a predetermined incident angle, and the second ultrasonic wave is oscillated by the ultrasonic oscillating and receiving unit toward the upper surface of the wafer in a direction perpendicular thereto. The reflected waves obtained by the reflection of the first and second ultrasonic waves in the wafer are received by the ultrasonic oscillating and receiving unit. The crack in the wafer is detected from the waveform information on the first ultrasonic wave, and the thickness of the wafer is detected from the waveform information on the second ultrasonic wave. Accordingly, the crack detection and the thickness detection for the wafer can be performed by the single apparatus. In addition, since the reflected waves obtained by the reflection of the first and second ultrasonic waves are received by the common ultrasonic oscillating and receiving unit, the number of parts can be reduced to thereby suppress an increase in equipment cost. Further, the ultrasonic oscillating and receiving unit alternately repeats the reception of the first ultrasonic wave and the reception of the second ultrasonic wave, so that the crack detection and the thickness detection for the wafer can be performed concurrently during grinding. Further, although a vertical crack is apt to generate in the wafer so as to extend from the upper surface to the lower surface of the wafer during grinding, such a vertical crack can be easily detected because the first ultrasonic wave propagates in a direction intersecting the direction of extension of the vertical crack.

Preferably, when there is a variation in the waveform information on the lower surface reflected wave received by the ultrasonic oscillating and receiving unit in calculating the thickness of the wafer, the thickness calculating unit determines that the crack is present in the wafer.

Preferably, the crack and thickness detecting apparatus further includes a waveform detecting unit detecting the waveform information on the first and second ultrasonic waves and a control unit controlling the pulse voltage generating unit and the waveform detecting unit. When the pulse voltage generating unit is controlled by the control unit to apply a pulse voltage to the ultrasonic oscillating unit, the waveform detecting unit is controlled by the control unit to transmit the waveform information detected to the crack determining unit, whereas when the pulse voltage generating unit is controlled by the control unit to apply a pulse voltage to the ultrasonic oscillating and receiving unit, the waveform detecting unit is controlled by the control unit to transmit the waveform information detected to the thickness calculating unit. When the pulse voltage generating unit applies a pulse voltage to the ultrasonic oscillating unit, the waveform detecting unit detects the waveform of a reflected wave obtained by the reflection of the first ultrasonic wave irregularly reflected on the crack in the wafer, whereas when the pulse voltage generating unit applies a pulse voltage to the ultrasonic oscillating and receiving unit, the waveform detecting unit detects the waveform of an upper surface reflected wave obtained by the reflection of the second ultrasonic wave reflected on the upper surface of the wafer and the waveform of a lower surface reflected wave obtained by the reflection of the second ultrasonic wave reflected on the lower surface of the wafer.

According to the present invention, the first ultrasonic wave is oscillated obliquely toward the upper surface of the wafer, and the second ultrasonic wave is oscillated perpendicularly toward the upper surface of the wafer. The reflected wave corresponding to the first ultrasonic wave and the reflected wave corresponding to the second ultrasonic wave are alternately received by the ultrasonic oscillating and receiving unit. Accordingly, the crack and thickness of the wafer can be detected during grinding by an inexpensive configuration.

The above and other objects, features and advantages of the present invention and the manner of realizing them will become more apparent, and the invention itself will best be understood from a study of the following description and appended claims with reference to the attached drawings showing some preferred embodiment of the invention.

DETAILED DESCRIPTION OF THE PREFERRED EMBODIMENT

Figure 1:
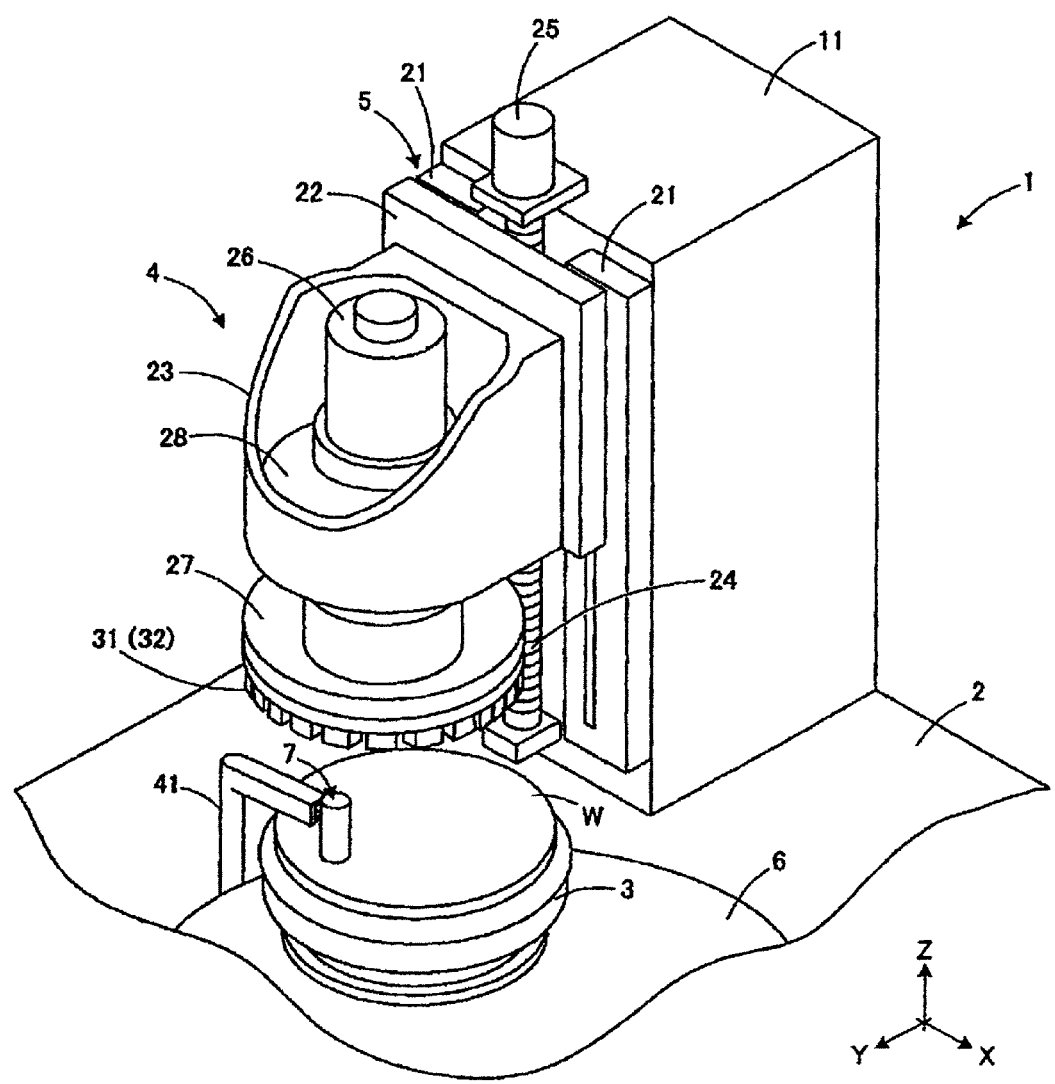
FIG. 1 is a perspective view of an essential part of a grinding apparatus.

There will now be described a crack and thickness detecting apparatus according to a preferred embodiment of the present invention with reference to the attached drawings. FIG. 1 is a perspective view of a grinding apparatus 1 including the crack and thickness detecting apparatus according to this preferred embodiment. The configuration of the grinding apparatus 1 shown in FIG. 1 is merely illustrative. That is, it is essential that the grinding apparatus 1 is so configured as to include a crack and thickness detecting apparatus for detecting a crack and thickness of a wafer during grinding.

As shown in FIG. 1, the grinding apparatus 1 includes a chuck table 3 for holding a wafer W and a grinding unit 4 having a grinding wheel 31 for grinding the wafer W. The chuck table 3 and the grinding wheel 31 are relatively rotated to grind the wafer W until the thickness of the wafer W is reduced to a desired thickness. The wafer W may be a semiconductor wafer formed of silicon (Si) or gallium arsenide (GaAs), for example, an inorganic material substrate formed of ceramic, glass, or sapphire ($Al_2O_3$), for example, a substrate formed of ductile materials such as platelike metal and resin, or a substrate formed of various work materials as required to have a TTV (Total Thickness Variation) on the order of micrometers to submicrometers.

The grinding apparatus 1 has a substantially boxlike base 2. A turn table 6 is rotatably provided on the upper surface of the base 2, and a plurality of chuck tables 3 (one of which being shown in FIG. 1) are arranged on the upper surface of the turn table 6. A support column 11 for supporting the grinding unit 4 is provided on the rear side of the turn table 6. Each chuck table 3 is rotatable on the upper surface of the turn table 6. A holding surface 15 (see FIG. 2) of porous ceramic material is formed on the upper surface of the chuck table 3. The holding surface 15 is connected through a passage (not shown) formed in the chuck table 3 to a vacuum source (not shown), thereby applying a vacuum to the holding surface 15 to hold the wafer W on the holding surface 15 under suction.

A crack and thickness detecting apparatus 7 for detecting a crack and thickness of the wafer W during grinding is provided in the vicinity of the turn table 6 on the upper surface of the base 2. The crack and thickness detecting apparatus 7 is pivotally supported through an inverted L-shaped supporting member 41 so as to be horizontally swingable above the chuck table 3. The crack and thickness detecting apparatus 7 is so configured as to oscillate an ultrasonic wave to the wafer W during grinding and detect a crack and thickness of the wafer W according to the waveform of a reflected wave from the wafer W. By detecting a crack in the wafer W, a position of device failure can be determined. Further, a grinding amount can be controlled according to the detected thickness of the wafer W. The configuration of the crack and thickness detecting apparatus 7 will be hereinafter described in more detail.

The support column 11 is provided with a feeding unit 5 for vertically moving the grinding unit 4. The feeding unit 5 includes a pair of parallel guide rails 21 provided on the front surface of the support column 11 so as to extend in the Z direction and a motor-driven Z-axis table 22 slidably supported to the guide rails 21. The grinding unit 4 is supported through a housing 23 on the front surface of the Z-axis table 22. A nut portion (not shown) is formed on the back surface of the Z-axis table 22, and a ball screw 24 is threadedly engaged with this nut portion of the Z-axis table 22. A drive motor 25 is connected to one end of the ball screw 24. By operating the drive motor 25, the ball screw 24 is rotated to thereby move the grinding unit 4 along the guide rails 21 in the Z direction.

The grinding unit 4 includes a cylindrical spindle 26 and a mount 27 provided at the lower end of the spindle 26. A flange 28 is formed so as to project radially outward from the spindle 26. The grinding unit 4 is supported through this flange 28 to the housing 23. The grinding wheel 31 is mounted on the lower surface of the mount 27. The grinding wheel 31 includes a plurality of abrasive members 32 arranged annularly. During grinding by the grinding apparatus 1, the thickness of the wafer W is detected in real time by the crack and thickness detecting apparatus 7, and the feed amount of the grinding unit 4 is controlled so that the detected thickness of the wafer W approaches a finished thickness. At the same time, a crack in the wafer W causing device failure is also detected, and an operator is alerted at the time the crack has been detected.

Figure 2:
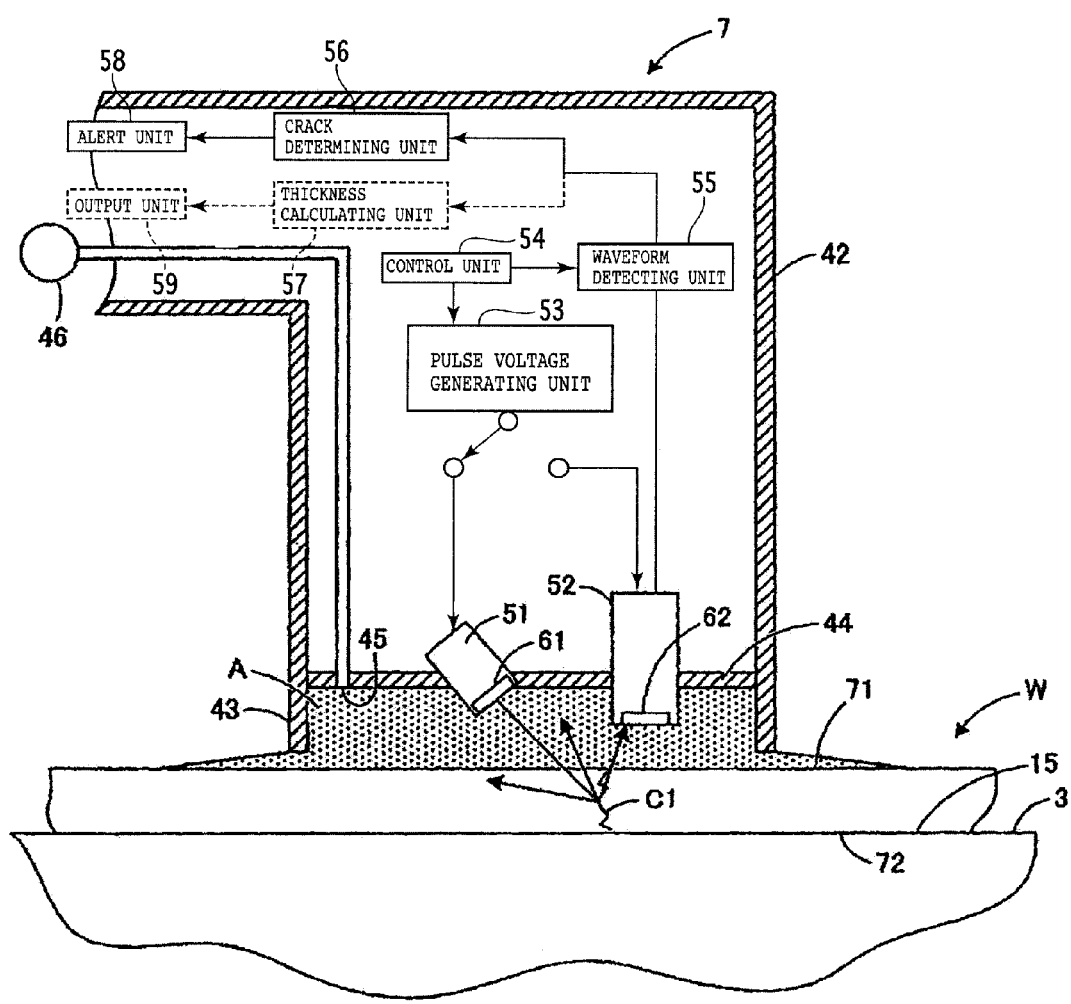
FIG. 2 is a block diagram showing a first condition of a crack and thickness detecting apparatus according to a preferred embodiment of the present invention in detecting a crack.

There will now be described the crack detection and the thickness detection by the crack and thickness detecting apparatus 7 with reference to FIGS. 2 to 7. As shown in FIG. 2, the crack and thickness detecting apparatus 7 has a cylindrical housing 42. The lower end of the housing 42 is adapted to come near an upper surface 71 of the wafer W held on the chuck table 3. In this condition, water A as an ultrasonic wave propagating medium is supplied to the upper surface 71 of the wafer W and an ultrasonic wave is oscillated. The housing 42 has a cylindrical wall 43 and a bottom plate 44 provided inside the cylindrical wall 43 at a position just above the lower end of the cylindrical wall 43, thereby forming a recess for storing the water A between the bottom plate 44 and the upper surface 71 of the wafer W. The bottom plate 44 is provided with an ultrasonic oscillating unit 51 and an ultrasonic oscillating and receiving unit 52. The ultrasonic oscillating unit 51 has an ultrasonic vibrator 61, and the ultrasonic oscillating and receiving unit 52 has an ultrasonic vibrator 62. These ultrasonic vibrators 61 and 62 are exposed to the upper surface 71 of the wafer W.

The ultrasonic oscillating unit 51 is obliquely mounted to the bottom plate 44, and the ultrasonic oscillating and receiving unit 52 is vertically mounted to the bottom plate 44. The ultrasonic oscillating unit 51 and the ultrasonic oscillating and receiving unit 52 are selectively connected to a pulse voltage generating unit 53. When a pulse voltage is applied from the pulse voltage generating unit 53 to the ultrasonic vibrator 61, the ultrasonic oscillating unit 51 oscillates a first ultrasonic wave to the upper surface 71 of the wafer W at a predetermined incident angle. On the other hand, when a pulse voltage is applied from the pulse voltage generating unit 53 to the ultrasonic vibrator 62, the ultrasonic oscillating and receiving unit 52 oscillates a second ultrasonic wave to the upper surface 71 of the wafer W in a direction perpendicular thereto.

The pulse voltage generating unit 53 is controlled by a control unit 54 to alternately switch the connection to the ultrasonic oscillating unit 51 or the ultrasonic oscillating and receiving unit 52. Accordingly, the first ultrasonic wave and the second ultrasonic wave are alternately oscillated from the ultrasonic oscillating unit 51 and the ultrasonic oscillating and receiving unit 52, respectively, to the upper surface 71 of the wafer W with a time difference. Further, the ultrasonic oscillating and receiving unit 52 functions not only to oscillate the second ultrasonic wave, but also to receive reflected waves obtained by the reflection of the first and second ultrasonic waves propagating in the wafer W. At this time, the ultrasonic oscillating and receiving unit 52 alternately receives the first ultrasonic wave and the second ultrasonic wave in synchronism with the switching of the pulse voltage applied from the pulse voltage generating unit 53.

When the ultrasonic oscillating and receiving unit 52 receives the reflected waves obtained by the reflection of the first and second ultrasonic waves, the ultrasonic oscillating and receiving unit 52 outputs waveform information on these reflected waves to a waveform detecting unit 55. The waveform detecting unit 55 includes an amplifier, A/D converter, filter, etc., thereby performing various kinds of processing to the waveform information, such as amplification, conversion from analog data to digital data, and noise elimination. Further, the waveform detecting unit 55 is controlled by the control unit 54 to alternately switch the connection to a crack determining unit 56 or a thickness calculating unit 57. When the pulse voltage from the pulse voltage generating unit 53 is applied to the ultrasonic oscillating unit 51, the waveform detecting unit 55 outputs the waveform information to the crack determining unit 56. On the other hand, when the pulse voltage from the pulse voltage generating unit 53 is applied to the ultrasonic oscillating and receiving unit 52, the waveform detecting unit 55 outputs the waveform information to the thickness calculating unit 57.

The crack determining unit 56 determines the crack in the wafer W according to information on irregular reflection included in the waveform information of the reflected wave obtained by the reflection of the first ultrasonic wave, and then outputs the result of determination to an alert unit 58. In the case that the crack is present in the wafer W, the alert unit 58 alerts the operator to the presence of the crack in the wafer W. The thickness calculating unit 57 calculates the thickness of the wafer W according to information on an upper surface reflected wave and a lower surface reflected wave included in the waveform information of the reflected wave obtained by the reflection of the second ultrasonic wave, and then outputs the result of calculation through an output unit 59 to the feeding unit 5 (see FIG. 1). The feeding unit 5 controls a grinding amount according to the calculated thickness of the wafer W.

The bottom plate 44 of the housing 42 is formed with a water supply opening 45 for the wafer A as an ultrasonic wave propagating medium. The water supply opening 45 is connected through a pipe provided in the housing 42 to a water source 46. When the water A is supplied from the water source 46, the space defined between the bottom plate 44 and the upper surface 71 of the wafer W is filled with the water A. Accordingly, the ultrasonic vibrators 61 and 62 of the ultrasonic oscillating unit 51 and the ultrasonic oscillating and receiving unit 52 are immersed in the water A stored in this apace, so that the first and second ultrasonic waves are applied to the upper surface 71 of the wafer W without passing through an air layer. Accordingly, it is possible to suppress the reflection of the first and second ultrasonic waves on the interface (upper surface 71) between the water layer and the wafer W, thereby improving the ability of propagation of the first and second ultrasonic waves into the wafer W.

There will now be described the crack detection for the wafer W during grinding with reference to FIG. 2. The cylindrical housing 42 is lowered to a position near the upper surface 71 of the wafer W in such a manner that the lower end of the cylindrical wall 43 of the housing 42 is positioned close to the upper surface 71 of the wafer W so as not to come into contact therewith. Accordingly, there is defined a space by the cylindrical wall 43, the bottom plate 44, and the upper surface 71 of the wafer W. Thereafter, the water A is supplied from the water source 46 through the water supply opening 45 into this space. As a result, the air inside this space is expelled from the gap between the lower end of the cylindrical wall 43 and the upper surface 71 of the wafer W, and this space between the bottom plate 44 and the upper surface 71 of the wafer W is filled with the water A. In this manner, a water tank is formed to immerse the ultrasonic vibrators 61 and 62 of the ultrasonic oscillating unit 51 and the ultrasonic oscillating and receiving unit 52 in the water A.

Thereafter, the pulse voltage generating unit 53 is controlled by the control unit 54 to apply a pulse voltage to the ultrasonic vibrator 61 of the ultrasonic oscillating unit 51. Accordingly, the first ultrasonic wave is oscillated from the ultrasonic vibrator 61 and obliquely applied to the upper surface 71 of the wafer W at a predetermined incident angle to propagate in the wafer W. The first ultrasonic wave propagating in the wafer W is irregularly reflected by a crack C1 generated in the wafer W during grinding. The reflected wave from the crack C1 is received by the ultrasonic oscillating and receiving unit 52. During grinding, a vertical load is applied downward from the grinding wheel 31 to the wafer W, so that a vertical crack is apt to generate so as to extend from the upper surface 71 to a lower surface 72 of the wafer W. Accordingly, by making the first ultrasonic wave obliquely propagate in the wafer W, the vertical crack C1 in the wafer W can be easily detected.

Figure 3A:
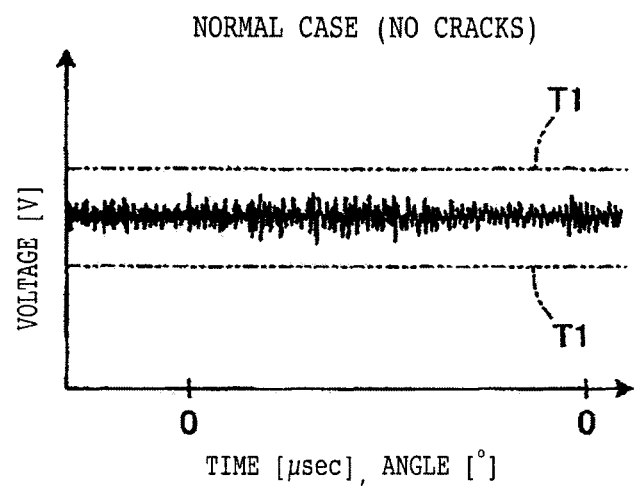
FIG. 3A is a graph showing waveform information on a reflected wave in the case that no cracks are detected.
Figure 3B:
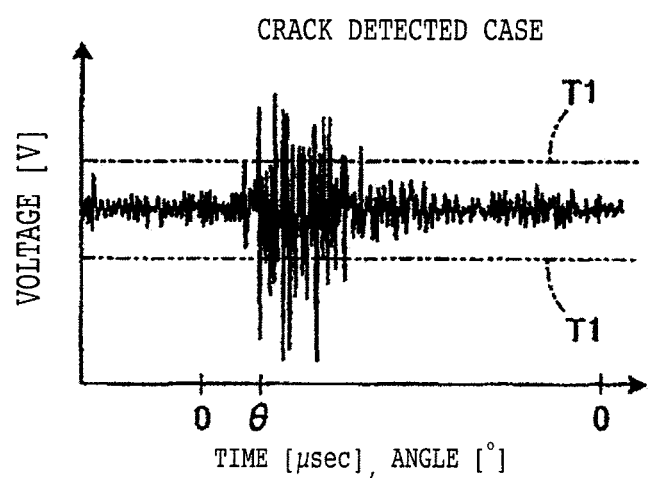
FIG. 3B is a graph showing waveform information on a reflected wave in the case that a crack is detected.

When the reflected wave obtained by the reflection of the first ultrasonic wave is received by the ultrasonic oscillating and receiving unit 52, an analog signal indicating the waveform information on this reflected wave is output from the ultrasonic oscillating and receiving unit 52 to the waveform detecting unit 55. In the waveform detecting unit 55, this analog signal is converted into a digital signal. Further, ambient noise included in the waveform information and the reflected waves from the upper surface 71 and the lower surface 72 of the wafer W are eliminated by the filter in the waveform detecting unit 55. As a result, the waveform information shown in FIGS. 3A and 3B is output from the waveform detecting unit 55 to the crack determining unit 56. In the case that the crack C1 is absent in the wafer W, the waveform information on the reflected wave obtained by the reflection of the first ultrasonic wave has a substantially constant and small amplitude as shown in FIG. 3A. On the other hand, in the case that the crack C1 is present in the wafer W, the waveform information on the reflected wave obtained by the reflection of the first ultrasonic wave has an amplitude temporarily largely changed as shown in FIG. 3B.

The crack determining unit 56 detects the crack C1 in the wafer W according to such a change in the waveform. For example, in the case that the waveform information on the reflected wave obtained by the reflection of the first ultrasonic wave has an amplitude greater than or equal to a threshold T1 as shown in FIG. 3B, the crack determining unit 56 determines that the crack C1 is present in the wafer W. As a modification, a reference position (0-degree position) of the chuck table 3 holding the wafer W may be detected by a zero-point sensor (not shown), and an angular position of the crack C1 in the wafer W with respect to the reference position of the chuck table 3 may be detected by the crack determining unit 56. In the case shown in FIG. 3B, the crack C1 in the wafer W is detected at an angular position corresponding to a rotational angle θ from the reference position. When the crack C1 in the wafer W is detected by the crack determining unit 56, the alert unit 58 alerts the operator to the presence of the crack C1 in the wafer W.

Figure 4:
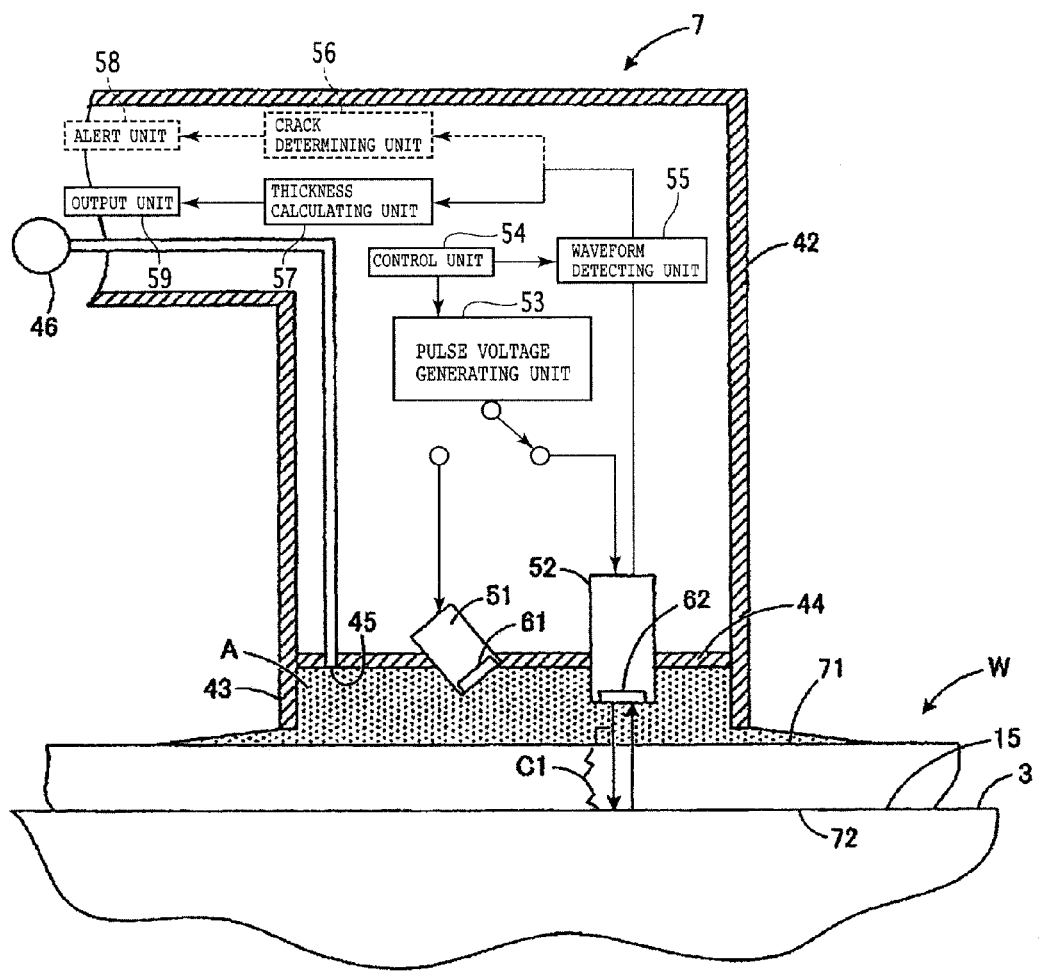
FIG. 4 is a block diagram showing a second condition of the crack and thickness detecting apparatus in detecting a thickness.

There will now be described the thickness detection for the wafer W during grinding with reference to FIG. 4. In detecting the thickness of the wafer W, the pulse voltage generating unit 53 is controlled by the control unit 54 to switch the connection from the ultrasonic oscillating unit 51 to the ultrasonic oscillating and receiving unit 52. In the condition where the space between the bottom plate 44 and the upper surface 71 of the wafer W is filled with the water A, a pulse voltage is applied from the pulse voltage generating unit 53 to the ultrasonic vibrator 62 of the ultrasonic oscillating and receiving unit 52. Accordingly, the second ultrasonic wave is oscillated by the ultrasonic vibrator 62 and then applied to the upper surface 71 of the wafer W in a direction perpendicular thereto to propagate in the wafer W.

Figure 5:
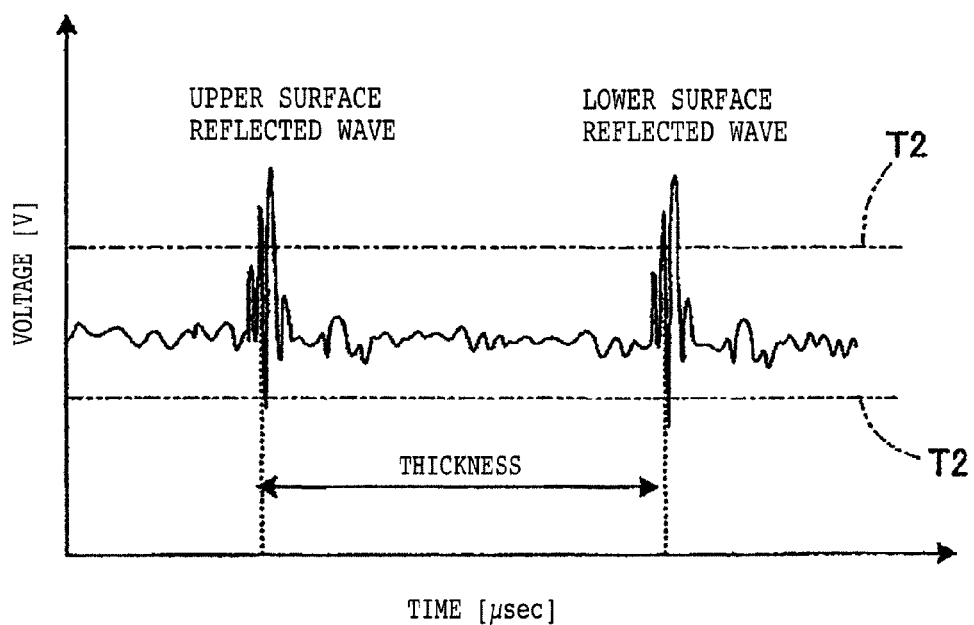
FIG. 5 is a graph showing waveform information on reflected waves in detecting a thickness.

The second ultrasonic wave is partially reflected on the upper surface 71 of the wafer W and then received as an upper surface reflected wave by the ultrasonic oscillating and receiving unit 52. The second ultrasonic wave passing through the upper surface 71 of the wafer W is reflected on the lower surface 72 of the wafer W and then received as a lower surface reflected wave by the ultrasonic oscillating and receiving unit 52. When the upper surface reflected wave and the lower surface reflected wave are received by the ultrasonic oscillating and receiving unit 52, they are output as an analog signal indicating waveform information to the waveform detecting unit 55. In the waveform detecting unit 55, this analog signal is converted into a digital signal. Further, ambient noise or the like included in the waveform information is eliminated by the filter in the waveform detecting unit 55. As a result, waveform information as shown in FIG. 5 is output to the thickness calculating unit 57. As apparent from FIG. 5, the waveform information on the reflected waves obtained by the reflection of the second ultrasonic wave has an amplitude temporarily largely changed in each of the upper surface reflected wave and the lower surface reflected wave.

The thickness calculating unit 57 detects the thickness of the wafer W according to a time difference between the upper surface reflected wave and the lower surface reflected wave. For example, the thickness of the wafer W is calculated from Eq. (1).

$$\text{Thickness} = \{(\text{lower surface reflection time [sec]} - \text{upper surface reflection time [sec]})/2\} \times \text{sound velocity in the medium [m/sec]} \quad (1)$$

In Eq. (1), the upper surface reflection time is the time when the upper surface reflected wave is received by the ultrasonic oscillating and receiving unit 52, and the lower surface reflection time is the time when the lower surface reflected wave is received by the ultrasonic oscillating and receiving unit 52. The upper surface reflected wave and the lower surface reflected wave are detected in the case that the waveform information on the reflected waves obtained by the reflection of the second ultrasonic wave has an amplitude greater than or equal to a threshold T2 as shown in FIG. 5.

For example, in the case that the lower surface reflection time is 1172 [μsec] and the upper surface reflected time is 1000 [μsec] in a silicon wafer, the sound velocity (propagation speed) in silicon as the medium is 8433 [m/sec], so that the thickness of the silicon wafer is calculated as 725 [μm]. When the thickness of the wafer W is calculated by the thickness calculating unit 57, the result of calculation is output through the output unit 59 to the feeding unit 5 (see FIG. 1), and a grinding amount is controlled according to this detected thickness of the wafer W.

As described above, the crack detection and the thickness detection for the wafer W are alternately performed in the crack and thickness detecting apparatus 7. In this case, the connection of the pulse voltage generating unit 53 to the ultrasonic oscillating unit 51 or the ultrasonic oscillating and receiving unit 52 is alternately switched with such timing that the waveform information produced in the waveform detecting unit 55 is not interrupted. For example, in the case that the rotational speed of the chuck table 3 is 300 [rpm], the connection of the pulse voltage generating unit 53 to the ultrasonic oscillating unit 51 or the ultrasonic oscillating and receiving unit 52 is alternately switched with a period of 0.5 [msec]. In this manner, the crack detection and the thickness detection for the wafer W are alternately performed, so that the crack detection and the thickness detection for the wafer W can be performed concurrently during grinding.

Figure 6:
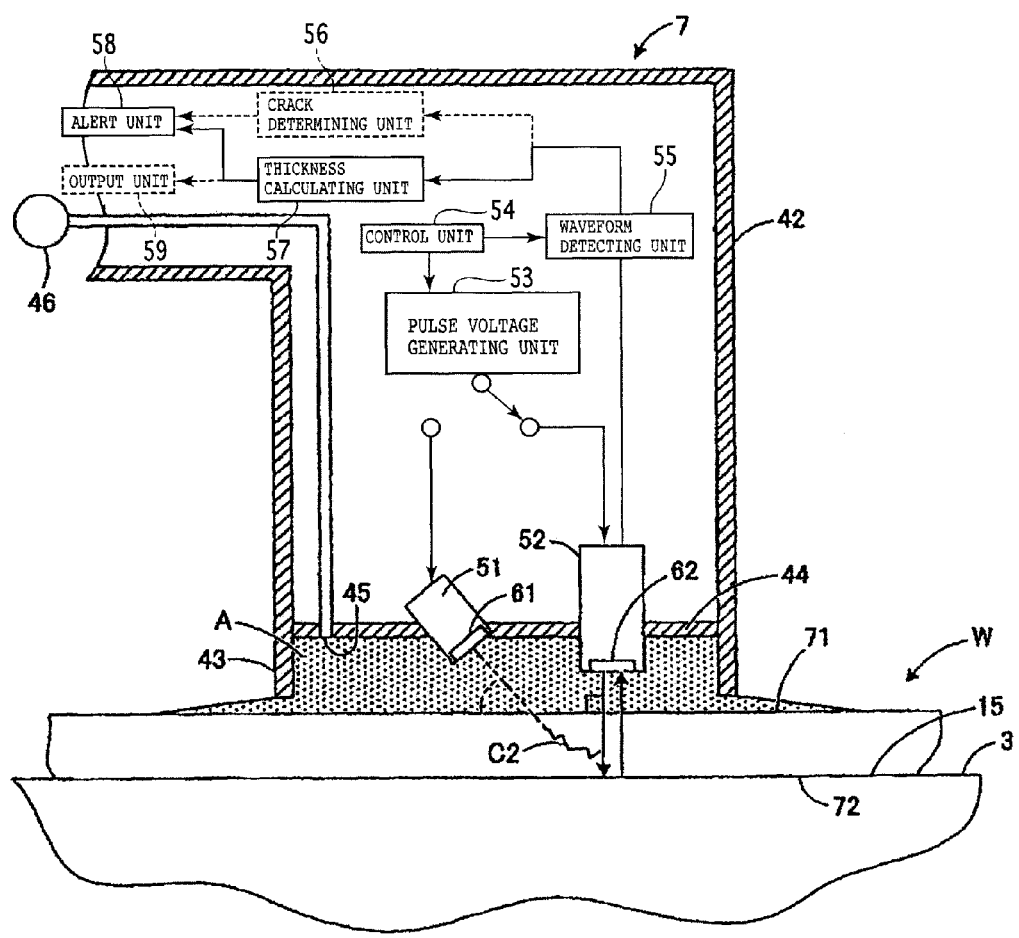
FIG. 6 is a block diagram showing a third condition of the crack and thickness detecting apparatus in the case that a crack is detected in detecting a thickness.

As shown in FIG. 6, there is a case that the direction of a crack C2 in the wafer W is the same as the direction of incidence of the first ultrasonic wave. In this case, the direction of the crack C2 in the wafer W is parallel to the direction of propagation of the first ultrasonic wave in the wafer W, so that the crack C2 in the wafer W cannot be detected by using the first ultrasonic wave. To cope with this case, variations in the waveform information on the lower surface reflected wave in performing the thickness detection are detected to thereby allow the detection of the crack C2 in the wafer W. When the second ultrasonic wave is oscillated from the ultrasonic vibrator 62, the second ultrasonic wave is applied to the upper surface 71 of the wafer W in a direction perpendicular thereto to propagate in the wafer W. Accordingly, the direction of propagation of the second ultrasonic wave in the wafer W intersects the direction of the oblique crack C2 in the wafer W.

Figure 7:
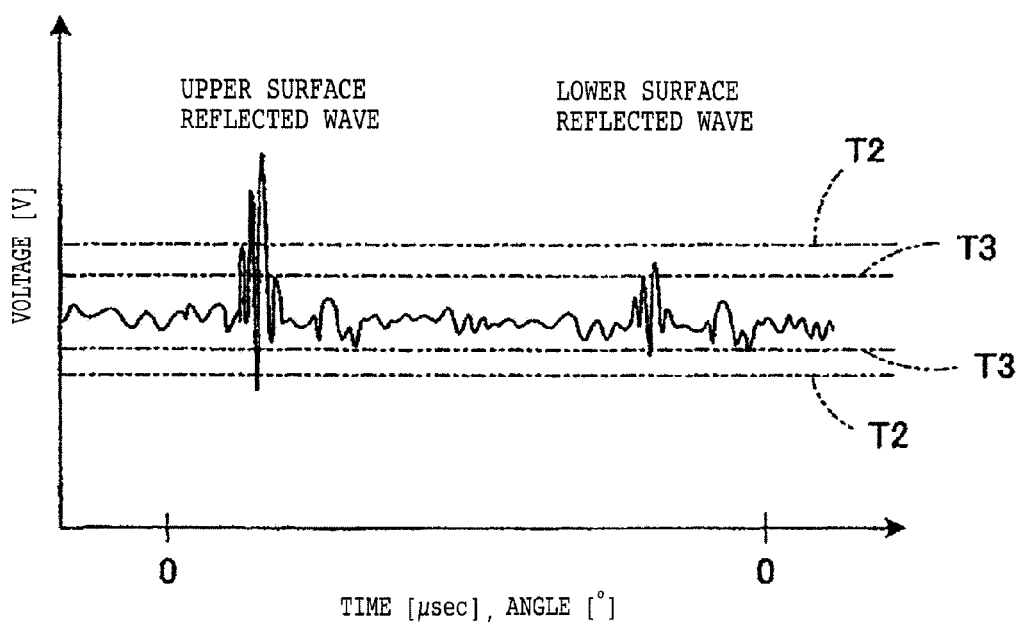
FIG. 7 is a graph showing waveform information on reflected waves in the case that a crack is detected in detecting a thickness.

The second ultrasonic wave is partially reflected on the upper surface 71 of the wafer W and then received as an upper surface reflected wave by the ultrasonic oscillating and receiving unit 52. The second ultrasonic wave passing through the upper surface 71 of the wafer W is irregularly reflected on the crack C2 in the wafer W and then received as a lower surface reflected wave by the ultrasonic oscillating and receiving unit 52. When the upper surface reflected wave and the lower surface reflected wave are received by the ultrasonic oscillating and receiving unit 52, these reflected waves are subjected to various kinds of processing in the waveform detecting unit 55 to obtain waveform information as shown in FIG. 7. This waveform information is next output to the thickness calculating unit 57. As apparent from FIG. 7, the waveform information on the reflected waves obtained by the reflection of the second ultrasonic wave has an amplitude temporarily largely changed in each of the upper surface reflected wave and the lower surface reflected wave.

As compared with the lower surface reflected wave shown in FIG. 5 where the crack C2 is absent, the lower surface reflected wave shown in FIG. 7 is varied in waveform. When such a change in the waveform of the lower surface reflected wave is detected by the thickness calculating unit 57, the crack C2 in the wafer W is detected rather than the thickness of the wafer W. For example, in the case that the amplitude of the lower surface reflected wave in the waveform information on the reflected waves obtained by the reflection of the second ultrasonic wave is greater than or equal to a threshold T3 and less than or equal to the threshold T2, it is determined that the crack C2 is present in the wafer W. As a modification, an angular position of the crack C2 in the wafer W with respect to the reference position (0-degree position) of the chuck table 3 may be detected by the thickness calculating unit 57 as in the case of the crack determining unit 56. When the crack C2 in the wafer W is detected by the thickness calculating unit 57, the connection of the thickness calculating unit 57 to the output unit 59 is switched to the alert unit 58, and the alert unit 58 alerts the operator to the presence of the crack C2 in the wafer W.

The crack and thickness detecting apparatus 1 starts to be driven simultaneously with the start of grinding of the wafer W. In detecting the crack and thickness of the wafer W, the crack and thickness detecting apparatus 7 is horizontally swung between a position near the center of the wafer W and the outer circumference of the wafer W. During grinding, the annular grinding surface of the grinding wheel 31 (see FIG. 1) is so positioned as to pass through the center of the wafer W. Accordingly, the crack and thickness detecting apparatus 7 cannot be positioned at the center of the wafer W. While the thickness of the wafer W can be detected at the outer circumference of the wafer W, the crack and thickness detecting apparatus 7 must be positioned at the center of the wafer W, so as to detect a crack at the center of the wafer W. Under these circumstances, the crack detection in an area except the center of the wafer W is performed during grinding, but the crack detection at the center of the wafer W is performed after grinding.

According to the crack and thickness detecting apparatus 7 described above, the first ultrasonic wave is oscillated from the ultrasonic oscillating unit 51 toward the upper surface 71 of the wafer W at a predetermined incident angle, and the second ultrasonic wave is oscillated from the ultrasonic oscillating and receiving unit 52 toward the upper surface 71 of the wafer W in a direction perpendicular thereto. The reflected waves obtained by the reflection of the first and second ultrasonic waves are received by the ultrasonic oscillating and receiving unit 52. A crack in the wafer W is detected from the waveform information on the first ultrasonic wave, and the thickness of the wafer W is detected from the waveform information on the second ultrasonic wave. Accordingly, the crack detection and the thickness detection for the wafer W can be performed by the single apparatus 7. In addition, since the reflected waves obtained by the reflection of the first and second ultrasonic waves are received by the common ultrasonic oscillating and receiving unit 52, the number of parts can be reduced to thereby suppress an increase in equipment cost. Further, the ultrasonic oscillating and receiving unit 52 alternately repeats the reception of the first ultrasonic wave and the reception of the second ultrasonic wave, so that the crack detection and the thickness detection for the wafer W can be performed concurrently during grinding. Further, although a vertical crack is apt to generate in the wafer W so as to extend from the upper surface 71 to the lower surface 72 of the wafer W during grinding, such a vertical crack can be easily detected because the first ultrasonic wave propagates in a direction intersecting the direction of extension of the vertical crack.

The present invention is not limited to the above preferred embodiment, but various modifications may be made. The size, shape, etc. of any part shown in the attached drawings are merely illustrative and they may be suitably changed within the scope where the effect of the present invention can be exhibited. Further, the above preferred embodiment may be suitably modified without departing from the scope of the object of the present invention.

For example, while the crack determining unit 56 determines that the crack C1 is present in the wafer W in the case that the waveform information on the reflected wave obtained by the reflection of the first ultrasonic wave has an amplitude greater than or equal to the threshold T1 (see FIG. 3B), the present invention is not limited to this configuration provided that the crack C1 in the wafer W can be detected. For example, in the case that the amplitude greater than or equal to the threshold T1 continues for a given period of time or more, the presence of the crack C1 may be determined.

Further, while the thickness calculating unit 57 determines that the crack C2 is present in the wafer W in the case that the lower surface reflected wave has an amplitude ranging from the threshold T3 to the threshold T2 (see FIG. 7), the present invention is not limited to this configuration provided that a change in amplitude of the lower surface reflected wave can be detected by the thickness calculating unit 57. For example, in the case that the amplitude ranging from the threshold T3 to the threshold T2 continues for a given period of time or more, the presence of the crack C2 may be determined.

According to the present invention, the crack and thickness of the wafer can be detected by an inexpensive configuration. In particular, the present invention is useful as a crack and thickness detecting apparatus to be mounted in a grinding apparatus for a semiconductor wafer.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A crack and thickness detecting apparatus for detecting a crack in a wafer held on a rotating chuck table and also detecting the thickness of said wafer, said crack and thickness detecting apparatus comprising:
    an ultrasonic oscillating unit oscillating a first ultrasonic wave toward the upper surface of said wafer held on the chuck table at a predetermined incident angle;
    an ultrasonic oscillating and receiving unit oscillating a second ultrasonic wave toward the upper surface of said wafer in a direction perpendicular thereto and also receiving said first ultrasonic wave and said second ultrasonic wave propagated and reflected in said wafer;
    a pulse voltage generating unit applying a pulse voltage to said ultrasonic oscillating unit and said ultrasonic oscillating and receiving unit;
    a crack determining unit determining whether or not the crack is present in said wafer from waveform information on said first ultrasonic wave received by said ultrasonic oscillating and receiving unit; and
    a thickness calculating unit calculating the thickness of said wafer from waveform information on said second ultrasonic wave received by said ultrasonic oscillating and receiving unit,
    wherein said ultrasonic oscillating unit and said ultrasonic oscillating and receiving unit alternately oscillate said first ultrasonic wave and said second ultrasonic wave to said wafer held on said rotating chuck table with a time difference, and said ultrasonic oscillating and receiving unit alternately receives said first ultrasonic wave and said second ultrasonic wave,
    said first ultrasonic wave oscillated by said ultrasonic oscillating unit and applied obliquely to said wafer is propagated in said wafer and irregularly reflected by the crack in said wafer, and said crack determining unit determines the presence of the crack in said wafer in the case that said ultrasonic oscillating and receiving unit receives a reflected wave obtained by the irregular reflection of said first ultrasonic wave, and
    said second ultrasonic wave oscillated by said ultrasonic oscillating and receiving unit and applied perpendicularly to said wafer is reflected on the upper surface of said wafer to generate an upper surface reflected wave, propagated in said wafer and also reflected on the lower surface of said wafer to generate a lower surface reflected wave, and said thickness calculating unit calculates the thickness of said wafer from a time difference between the reception of said upper surface reflected wave and the reception of said lower surface reflected wave by said ultrasonic oscillating and receiving unit.

2. The crack and thickness detecting apparatus according to claim 1, wherein when there is a variation in the waveform information on said lower surface reflected wave received by said ultrasonic oscillating and receiving unit in calculating the thickness of said wafer, said thickness calculating unit determines that the crack is present in said wafer.

3. The crack and thickness detecting apparatus according to claim 1, wherein the ultrasonic oscillating unit comprises an ultrasonic vibrator that is obliquely mounted with respect to the upper surface of the wafer.

* * * * *